US010660336B2

(12) United States Patent
Lee et al.

(10) Patent No.: US 10,660,336 B2
(45) Date of Patent: May 26, 2020

(54) METHOD FOR CONTROLLING PLANT VIRUSES USING ANTIVIRAL COMPOSITION COMPRISING TRICHODERMIN

(71) Applicants: SEOUL WOMEN'S UNIVERSITY INDUSTRY-UNIVERSITY COOPERATION FOUNDATION, Seoul (KR); KOREA UNIVERSITY RESEARCH AND BUSINESS FOUNDATION, Seoul (KR)

(72) Inventors: Dong Ho Lee, Seoul (KR); Jae Jin Kim, Seoul (KR); Ki Hyun Ryu, Namyangju-si (KR); Beom Seok Kim, Seoul (KR); Seung Mok Ryu, Seoul (KR)

(73) Assignees: SEOUL WOMEN'S UNIVERSITY INDUSTRY-UNIVERSITY COOPERATION FOUNDATION, Seoul (KR); KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 0 days.

(21) Appl. No.: 16/221,348

(22) Filed: Dec. 14, 2018

(65) Prior Publication Data

US 2019/0104739 A1 Apr. 11, 2019

Related U.S. Application Data

(62) Division of application No. 15/032,611, filed as application No. PCT/KR2015/013238 on Dec. 4, 2015, now abandoned.

(30) Foreign Application Priority Data

Dec. 4, 2014 (KR) ........................ 10-2014-0172861

(51) Int. Cl.

| | |
|---|---|
| *A01N 43/90* | (2006.01) |
| *C12P 17/16* | (2006.01) |
| *A01N 63/10* | (2020.01) |
| *A01N 63/30* | (2020.01) |
| *C05G 3/60* | (2020.01) |
| *C07D 493/08* | (2006.01) |
| *C12R 1/885* | (2006.01) |

(52) U.S. Cl.
CPC ............. *A01N 43/90* (2013.01); *A01N 63/10* (2020.01); *A01N 63/30* (2020.01); *C05G 3/60* (2020.02); *C07D 493/08* (2013.01); *C12P 17/162* (2013.01); *C12R 1/885* (2013.01)

(58) Field of Classification Search
None
See application file for complete search history.

(56) References Cited

U.S. PATENT DOCUMENTS

| | | | |
|---|---|---|---|
| 5,157,104 A | 10/1992 | Sivam et al. |
| 8,026,410 B2 | 9/2011 | Tumer et al. |
| 2007/0093387 A1 | 4/2007 | Sumi et al. |
| 2014/0013470 A1 | 1/2014 | Tumer et al. |

FOREIGN PATENT DOCUMENTS

| | | |
|---|---|---|
| CN | 101057593 A | 10/2007 |
| CN | 101429203 A | 5/2009 |
| CN | 101787031 A | 7/2010 |
| JP | 46-032799 | 9/1971 |
| JP | 62-181280 | 8/1987 |
| JP | 2004-131422 A | 4/2004 |
| JP | 4883500 B2 | 2/2012 |
| KR | 10-2006-0015600 A | 2/2006 |

OTHER PUBLICATIONS

Xu, X. et al. Synthesis and Antifungal Activities of Trichodermin Derivatives as Fungicides on Rice. Chemistry & Biodiversity 10(4) 600-611, Apr. 2013. (Year: 2013).*
MacIntyre G. et al. Hygromycin B Inhibits Synthesis of Murine Coronavirus RNA. Antimicrobial Agents and Chemotherapy 35(12) 2630-2633, Dec. 1991. (Year: 1991).*
Swanstrom, R. et al. Restricted Transcription of the Herpes Simplex Virus Genome Occurring Early After Infection and in the Presence of Metabolic Inhibitors. Virology 66(1)140-150, Jul. 1975. (Year: 1975).*
Ayer & Miao 1992 "Secondary metabolites of the aspen fungus *Stachybotrys cylindrospora*" 71: 487-493.
Bissett, et al. 2015 "Accepted *Trichoderma* names in the year 2015" *IMA Fungus* 6(2): 263-295.
Japanese Office Action in related application No. JP-2016-525004, dated Apr. 18, 2017.
MacIntyre, et al. 1991 "Hygromycin B inhibits synthesis of murine coronavirus RNA" *Antimicrobial Agents and Chemotherapy* 35(12): 2630-2633.
Ryu, et al. 2017 "Antiviral activities of trichothecenes isolated from *Trichoderma albolutescens* against Pepper Mottle Virus" *J. Agric. Food Chem.* 65: 4273-4279.
Xu, et al. 2013 "Synthesis and antifungal activities of trichodermin derivatives as fungicides on rice" *Chemistry & Biodiversity* 10: 600-611.
KR Office Action, KR Patent Application No. 2014-0172861, dated Jun. 30, 2016.
Spak, J., et al., "New in vitro method for evaluating antiviral activity of acyclic nucleoside phosphonates against plant viruses," Antiviral Research 88 (2010), pp. 296-303.
Swanstrom, Ronald I., et al., "Restricted Transcription of the Herpes Simplex virus Genome Occurring Early After Infection and in the Presence of Metabolic Inhibitors," Virology 66, pp. 140-150 (1975).

* cited by examiner

*Primary Examiner* — Ralph J Gitomer
(74) *Attorney, Agent, or Firm* — Knobbe, Martens, Olson & Bear, LLP

(57) ABSTRACT

A method for controlling plant viruses comprising treating plant or soil with a composition for controlling plant viruses comprising Trichodermin wherein the composition has antiviral activity against plant viruses when applied to a plant or to soil. In some embodiments, the Trichodermin is isolated from a *Trichoderma albolutescens* strain.

7 Claims, 4 Drawing Sheets

Specification includes a Sequence Listing.

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
agcagctcaa gatcagacac                    20

<210> SEQ ID NO 2
<211> LENGTH: 21
<212> TYPE: DNA
<213> ORGANISM: Artificial Sequence
<220> FEATURE:
<223> OTHER INFORMATION: primer

<400> SEQUENCE: 2
catatttctg accccaagca g                  21

METHOD FOR CONTROLLING PLANT VIRUSES USING ANTIVIRAL COMPOSITION COMPRISING TRICHODERMIN

CROSS REFERENCE TO RELATED APPLICATION(S)

This application is a divisional application of U.S. application Ser. No. 15/032,611, filed Apr. 27, 2016, which is the U.S. National Phase of International Application PCT/KR2015/013238 filed Dec. 4, 2015 and designating the U.S., which claims the benefit under 35 USC § 119(a) of Korean Patent Application No. 10-2014-0172861 filed on Dec. 4, 2014 in the Korean Intellectual Property Office, the entire disclosures of which are incorporated herein by reference for all purposes.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 29607349_1.TXT, the date of creation of the ASCII text file is Dec. 14, 2018, and the size of the ASCII text file is 994 bytes.

BACKGROUND

1. Field

The following description relates to an antiviral composition and a composition for controlling plant viruses comprising an active component of Trichodermin or Trichoderminol isolated from *Trichoderma albolutescens* strain, and a method for controlling plant viruses using the composition.

2. Description of Related Art

A virus can infect all types of life forms that replicates only inside the host cells of other organisms. The virus can be classified into animal viruses, plant viruses, bacterial viruses, fungal viruses and the like based on host cells.

The plant viruses are viruses that affect plants. Unlike fungi having complete unit of living organisms, the plant viruses are non-cellular, abiotic and do not have their own metabolism since they do not have enzymes. Since the plant viruses replicate using host cells, they damage various types of plants. It is therefore difficult for antiviral therapies to inhibit only viral functions since the plant viruses share host cellular processes (Yanmei Li et al., Proc. Natl. Acad. Sci. U.S.A 104:8083-8088, 2007). Thus, even though the plant virus was discovered in 1890s, development of antiviral agent on plant virus diseases is still incomplete, except physical or indirect control methods, for example, removal of an infected plant from its field or control of an insect vector, etc.

Research is currently under way on metabolites from plants having antiviral activity against a tobacco mosaic virus (TMV). Activities of alkaloids from Picrasma quassioides, quassinoids from Brucea javanica, flavonoids from Cassia fistula, chromones from Cassia siamea have been reported (Jia Chen et al., J. Agric, Food Chem. 57:6590-9595, 2009; Xiao-Hui Yan et al., J. Agric, Food Chem. 58:1572-1577, 2010; Wei Zhao et al., Phytochem. Lett. 179-182, 2013; Qiu-Fen Hu et al., J. Nat. Prod. 75:1909-1914, 2012). However, this has only verified anti-viral activities of these compounds against the tobacco mosaic virus but there is still limit on their applications.

Accordingly, inventors of this disclosure have isolated and identified a tricothecene-based compound of Trichodermin or Trichoderminol from *Trichoderma albolutescens* strain and further found that this compound shows excellent antiviral activity against a tobacco mosaic virus which is a representative plant virus and a pepper mottle virus which causes disease symptom to a systemic host.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

According to one general aspect, there are provided an antiviral composition and a composition for controlling plant viruses.

According to another general aspect, there is provided a method for controlling plant viruses using the composition.

According to another general aspect, there are provided a pesticidal composition and a composition for fertilizer additives including the composition with antifungal activity against plant viruses.

An antiviral composition according to an example includes Trichodermin or Trichoderminol as an active component.

A composition for controlling plant viruses according to an example includes Trichodermin or Trichoderminol as an active component.

A method for controlling plant viruses according to an example includes treating the composition in plant or soil.

A pesticidal composition having antifungal activity against plant viruses according to an example includes the composition.

A composition for fertilizer additives having antifungal activity against plant viruses according to an example includes the composition.

A composition for controlling plant viruses according to an example includes a microbial cell or a culture medium of *Trichoderma albolutescens*, or a mixture thereof. A method for controlling plant viruses according to an example includes treating a composition for controlling plant viruses including a microbial cell or a culture medium of *Trichoderma albolutescens*, or a mixture thereof in plant or soil.

A method for producing Trichodermin or Trichoderminol according to an example includes extracting Trichodermin or Trichoderminol from a microbial cell or a culture medium of *Trichoderma albolutescens*, or a mixture thereof.

A *Trichoderma albolutescens* KUC21115 strain (*Trichoderma albolutescens* KUC21115, Deposit No. KACC93215P) according to an example produces Trichodermin or Trichoderminol.

Trichodermin or Trichoderminol which is a tricothecene-based compound and is isolated from *Trichoderma albolutescens* strain shows an anti-viral activity against various plant viruses and is thus useful for controlling plant viruses. This description can facilitate mass production of an active component derived from natural products, provide environment-friendly antifungal agents, which do not harm plants, using safe materials, and be variously utilized in agricultural fields, for example, such as production of high-value crops.

Other features and aspects will be apparent from the following detailed description, the drawings, and the claims.

DEPOSIT OF BIOLOGICAL MATERIAL

The following biological material has been deposited in accordance with the terms of the Budapest Treaty with the Korean Agricultural Collection Center, Manassas, Va., on the date indicated:

| Biological material | Accession No. | Date |
| --- | --- | --- |
| *Trichoderma albolutescenes*, strain KUC21115 | KACC93215P | Oct. 1, 2014 |

*Trichoderma albolutescens*, strain KUC21115, was deposited as Accession No. KACC93215P on Oct. 1, 2014 with the Korean Agricultural Collection Center, 370 Nongsaengmyeong-ro, Wansan-gu, Jeonju, Jeollabuk-do, Republic of Korea (54874). This deposit was made under the provisions of the Budapest Treaty on the International Recognition of the Deposit of Microorganisms for the Purposes of Patent Procedure and the Regulations there under (Budapest Treaty). This assures maintenance of a viable culture of the deposit for 30 years from date of deposit. The deposit will be made available by the Korean Agricultural Collection Center under the terms of the Budapest Treaty, and subject to an agreement between Applicant and the Korean Agricultural Collection Center, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC § 122 and the Commissioner's rules pursuant thereto (including 37 CFR § 1.14). Availability of the deposited biological material is not to be construed as a license to practice the invention in contravention of the rights granted under the authority of any government in accordance with its patent laws.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. The sequences of operations described herein are merely examples, and are not limited to those set forth herein, but may be changed as will be apparent to one of ordinary skill in the art, with the exception of operations necessarily occurring in a certain order. Also, descriptions of functions and constructions that are well known to one of ordinary skill in the art may be omitted for increased clarity and conciseness. The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

An antiviral composition may include Trichodermin represented by the following Formula 1 or Trichoderminol represented by the following Formula 2 as an active component.

Formula 1

Formula 2

A composition for controlling plant viruses may include Trichodermin represented by Formula 1 or the Trichoderminol represented by Formula 2 as an active component.

Trichodermin or Trichoderminol according to an example may be isolated from *Trichoderma albolutescens* strain, particularly *Trichoderma albolutescens* strain with Deposit No. KACC93215P. Trichodermin or Trichoderminol may be also synthesized by methods known in the art. However, the method for preparing Trichodermin or Trichoderminol is not limited thereto.

Examples of plant viruses may include a tobacco mosaic virus (TMV), a pepper mottle virus (PepMoV), a cucumber mosaic virus (CMV), a pepper mild mottle virus (PMMoV), a zucchini yellow mosaic virus (ZYMV), a watermelon mosaic virus (WMV), a watermelon mosaic virus 2 (WMV2), a potato virus Y (PVY), a turnip mosaic virus (TuMV), a melon necrotic spot carmovirus (MNSV), a cucumber green mottle mosaic virus (CGMMV), a zucchini green mottle mosaic virus (ZGMMV), a potato leafroll virus (PLRV), a lily mottle virus (LMoV), a lily symptomless virus (LSV), an odontoglossum ringspot virus (ORSV), a cymbidium mosaic virus (CyMV), a broad bean wilt virus (BBWV), a tomato ringspot virus (TomRSV), a tobacco ringspot virus (TRSV), a tomato spotted wilt virus (TSWV), a strawberry mottle virus (SMoV) and a cactus X virus (CVX). However, the plant virus is not limited thereto.

Trichodermin or Trichoderminol according an example, which is a tricothecene-based compound and is isolated from *Trichoderma albolutescens* strain, shows an anti-viral activity against various plant viruses and is thus utilized as a composition for preventing or treating plant virus diseases caused by plant viruses.

A composition for controlling plant viruses according an example may include a microbial cell or a culture medium of *Trichoderma albolutescens*, or a mixture thereof.

A microbial cell or a culture medium of *Trichoderma albolutescens*, or a mixture thereof has an anti-viral activity against various plant viruses and is thus utilized as a composition for preventing or treating plant virus diseases caused by plant viruses.

The composition for controlling plant viruses may further include one or more materials having an anti-viral activity which are known in the art in addition to the active component of Trichodermin or Trichoderminol.

The composition for controlling plant viruses may be formulated in various forms known in agricultural fields. Formulation methods which are typically used in agricultural fields may be used. The composition may be formulated into solutions, granules, powders, emulsions, oil solutions, wettable powders or pastes. However, it is not limited thereto.

The composition for controlling plant viruses may include various components for the formulation, for example, such as a liquid carrier, a solid carrier, a surfactant, an adjuvant and the like.

The liquid carrier may include water, vegetable oil, ethanol and the like and the vegetable oil may include soybean oil, rapeseed oil, palm oil, palm kernel oil, rice bran oil, corn oil, palm oil, olive oil and the like. However, they are not limited thereto.

The solid carrier may include mineral powder, gelatin, alginic acid and the like. However, it is not limited thereto.

The mineral powder may include cation clay, bentonite, kaolin, talc, diatomaceous earth and the like. However, it is not limited thereto.

The surfactant may include ethyleneoxide, diethanolamine, sorbitol, glycerine and the like. However, it is not limited thereto.

The adjuvant may include diluent, antifreezing liquid, solvent, thickener, speader and the like. However, it is not limited thereto.

A concentration of Trichodermin or Trichoderminol included in the composition for controlling plant viruses may be controlled appropriately by one of ordinary skill in the art based on degree of plant growth, farmland environment, degree of plant virus diseases or the like. However, it is not limited thereto.

A method for controlling plant viruses according to an example may include treating the composition in plant or soil.

A method for controlling plant viruses according to an example may include treating the composition for controlling plant viruses including a microbial cell or a culture medium of *Trichoderma albolutescens*, or a mixture thereof in plant or soil.

The treating may include foliar treatment, soil treatment, immersion treatment, cutting branches or treatment useful for disinfecting farm equipments. However, it is not limited thereto.

A pesticidal composition having an antifungal activity against plant viruses may include the composition.

A composition for fertilizer additives having an antifungal activity against plant viruses may include the composition.

Trichodermin or Trichoderminol, which is a tricothecene-based compound isolated from *Trichoderma albolutescens* strain, has antiviral activities against various plant viruses and is thus added into pesticides, fertilizers or the like for preventing or treating plant virus diseases caused by plant viruses.

The pesticidal composition or the composition for fertilizer additives may further include one or more materials, for example, such as solvent, carrier, emulsifying agent, dispersing agent, adjuvant or the like, which are known in the art, in addition to the active component of Trichodermin or Trichoderminol. However, it is not limited thereto.

A method for producing Trichodermin or Trichoderminol may include extracting Trichodermin or Trichoderminol from a microbial cell or a culture medium of *Trichoderma albolutescens*, or a mixture thereof.

The extracting Trichodermin or Trichoderminol may be performed by various methods known in the art. However, the method is not limited particularly. A detail extracting method will be described in Examples below.

A *Trichoderma albolutescens* KUC21115 strain (*Trichoderma albolutescens* KUC21115, Deposit No. KACC93215P) may produce Trichodermin or Trichoderminol.

Hereinafter, although more detailed descriptions will be given by examples, those are only for explanation and there is no intention to limit the disclosure.

Example 1. Cultivation of *Trichoderma albolutescens* Strain and Isolation of Compounds from Extract Example 1-1. Cultivation and Extraction of *T. albolutescens* Strain

*Trichoderma albolutescens* strain was collected and identified from soil of Odaesan National Park by Professor Jae-Jin Kim (The RDA-Gene bank Information Center, National Institute of Agricultural Science of Rural Development Administration, Deposit No.: KACC93215P).

*T. albolutescens* strain was cultivated in potato dextrose agar (PDA) at a temperature of 28° C. in dark condition for 10 days. The *T. albolutescens* strain was extracted with 2 L of methanol 3 times and filtered. The filtrate was evaporated using a vacuum vapor compression concentrator to remove the solvent. The concentrated *T. albolutescens* methanol extract was suspended in distilled water and extracted with ethyl acetate. The separated ethyl acetate layer was filtered and concentrated to provide 0.8 g of *T. albolutescens* ethyl acetate extract.

Example 1-2. Isolation of Compounds 0.8 g of *T. albolutescens* ethyl acetate extract prepared in Example 1-1 was placed on a reversed phase silica gel (ODS-A, 12 nm, S-75 μm) column chromatography (3×58 cm) and eluted with a solvent composition of methanol-distilled water (MeOH:H$_2$O, 5:5, 8:2, 10:0) to obtain 6 fractions (fractions 1-6).

A fraction 2 (100 mg) from the 6 fractions was placed on a normal phase silica gel (silica gel 60, 230-400 Mesh) column chromatography (1×28 cm) and then eluted with a solvent composition of chloroform-methanol (CHCl$_3$:MeOH, 9.8:0.2, 9.5:0.5, 9:1, 7:3) to obtain 3 fractions (fraction 2-1 to fraction 2-3). A fraction 2-1 (30 mg) was placed on a normal phase silica gel (silica gel 60, 230-400 Mesh) column chromatography (1×38 cm) and then eluted with a solvent composition of hexane-ethyl acetate (hexane:EtOAc, 8:2, 7:3, 5:5) to obtain compound 2 (10 mg).

A fraction 3 (300 mg) was placed on a normal phase silica gel (silica gel 60, 230-400 Mesh) column chromatography (1×12 cm) and then eluted with a solvent composition of hexane-ethyl acetate (hexane:EtOAc, 8:2, 6:4, 5:5) to obtain compound 1 (200 mg)

Example 2. Structural Analysis of Compounds Isolated from *T. albolutescens* Strain Structural analysis of compounds 1 and 2 prepared in Example 1 was performed using following equipments.

A JASCO P-2000 polarimeter, a Varian 640-IR spectrometer for IR spectra, and a Varian 500 MHz NMR for $^1$H, $^{13}$C, and 2D NMR spectra were used. TMS-including CDCl$_3$ was used as an internal standard reference material. Chemical shift was represented by δ values. A Waters Q-TOF mass spectroscopy was used for high-resolution electrospray ionization mass spectra.

The compound 1 was identified as Trichodermin (Formula 1) and the compound 2 as Trichoderminol (Formula 2). Experimental results and structures of compounds are as follows.

Trichodermin: colorless, odorless and in an oil form. An optical rotational angle was $[\alpha]^{26}_D$-85.2 (c 1.5, CHCl$_3$), Vmax values were observed at 2963, 1730, 1436, 1373, 1240, 1078, 1029, 990 cm$^{-1}$ from IP spectra. Table 1 shows $^1$H and $^{13}$C NMR spectra analysis result (500 MHz, CDCl$_3$). 293.1762 [M+H]$^+$ (C$_{17}$H$_{25}$O$_4$, calculated 293.1753) was determined with a positive high resolution ESIMS and there is no negative ion detected with a negative ESIMS.

Formula 1

Trichoderminol: colorless, odorless and in an oil form. An optical rotational angle was $[\alpha]^{26}_D$-5.7 (c 0.8, CHCl$_3$). Vmax values were observed at 3444, 2928, 1725, 1433, 1375, 1245, 1074, 1030, 963 cm$^{-1}$ from IP spectra. Table 1 shows $^1$H and $^{13}$C NMR spectra analysis result (500 MHz, CDCl$_3$). 309.1 [M+H]$^+$, 617.3 [2M+H]$^+$, 925.5 [3M+H]$^+$ were determined with a positive ESIMS, 309.1694 [M+H]$^+$ (C$_{17}$H$_{25}$O$_5$, calculated 309.1702) with a high resolution ESIMS, and 353.1 [M+HCOO]$^-$ was determined with a negative ESIMS.

Formula 2

TABLE 1

NMR spectrum analysis result of Trichodermin and Trichoderminol isolated from Trichoderma albolutescenes (T. albolutescens) strain.

| Position | Trichodermin(1) $\delta_C$, type | $\delta_H$ (J in Hz) | HMBC$^a$ | Trichodermin(2) $\delta_C$, type | $\delta_H$ | HMBC$^a$ |
|---|---|---|---|---|---|---|
| 1 | O | | | O | | |
| 2 | 78.9 CH | 3.81, d(55) | 4, 5, 11, 12 | 79.3 CH | 3.82, d(55) | 4, 5, 11, 12 |
| 3 | 36.5$^b$ CH$_2$ | 1.91-2.01, m | 4, 5, 11, 12 | 36.7 CH$_2$ | 1.99, m | 2, 4 |
| | | 2.53, dd(8.0, 15.5) | 2, 5, 12 | | 2.54, dd(8.0, 15.5) | 2, 12 |
| 4 | 74.9 CH | 5.56, dd(3.5, 8.0) | 6, 12, CH$_3$COO | 75.0 CH | 5.58, dd(3.5, 8.0) | 12 |
| 5 | 48.8 C | | | 49.0 C | | |
| 6 | 40.2 C | | | 40.9 C | | |
| 7 | 24.3$^b$ CH$_2$ | 1.14, m | 6, 8, 11 | 24.1 CH$_2$ | 1.48, m | 6, 8, 9, 11 |
| | CH$_2$ | 1.91-2.01, m | | | 1.93, m | 6, 8, 9, |
| 8 | 27.8$^b$ CH$_2$ | 1.91-2.01, m | | 23.4 CH$_2$ | 2.09, m | 7, 9 |
| 9 | 139.8 C | | | 143.0 C | | |
| 10 | 118.6 CH | 5.40, m | 6, 8, 11, 16 | 118.6 CH | 5.69, m | 6 |
| 11 | 70.4 CH | 3.60, br d(5.5) | 7, 9, 10, 15 | 70.0 CH | 3.67, br d(5.5) | 9, 10 |
| 12 | 65.3 C | | | 65.5 C | | |
| 13 | 47.6 CH$_2$ | 2.82, d(4.0) | 12 | 47.8 CH$_2$ | 2.84, d(4.0) | 12 |
| | | 3.11, d(4.0) | 2, 12 | | 3.12, d(4.0) | 12 |
| 14 | 5.6 CH$_3$ | 0.71, s | 4, 5, 6, 12 | 5.8 CH$_3$ | 0.73, s | 4, 5, 6, 12 |
| 15 | 15.8 CH$_3$ | 0.93, s | 5, 6, 7, 11 | 16.0 CH$_3$ | 0.95, s | 5, 6, 7, 11 |
| 16 | 23.0 CH$_3$ | 1.71, s | 8, 9, 10 | | | |
| CH$_3$COO | 20.9 CH$_3$ | 2.07, s | CH$_3$COO | 21.1 CH$_3$ | 2.09, s | CH$_3$COO |
| CH$_3$COO | 170.7 C | | | 171.0 C | | |
| CH$_2$OH | | | | 66.2 CH$_2$ | 4.05, br d(14.0) | 8, 9, 10 |

$^a$HMBC correlation.
$^b$Interchangeable within the same column.

Example 3. Analysis of Anti-Viral Activity Against Pepper Mottle Virus

Example 3-1. Materials

*Nicotiana benthamiana* and *Capsicum anuum* L. were used as experiment host plant and provided from a plant virus genebank, Seoul women's university in order to determine an anti-viral activity against pepper mottle virus (PepMoV). A green fluorescent protein (GFP)-tagged pepper mottle virus was used to determine an anti-viral activity inside systemic host (Lee, M. Y et al., Virus Res. 155:487-494, 2011).

Example 3-2. Anti-Viral Activity at *Nicotiana benthamiana*

The following experiment was carried out to determine an anti-viral activity of the compounds prepared in Example 2 against the pepper mottle virus.

The *Nicotiana benthamiana*, which was used as a systemic host, was cultivated in a greenhouse at a temperature of 25° C. for 4 weeks after sowing. Pepper mottle virus-infected *Nicotiana benthamiana* leaves in which a green fluorescent protein is evenly spread on UV image were collected and ground with a 0.01 M phosphate buffered saline buffer (pH 7.2). This solution was used as an inoculum. Each compound sample was prepared by dissolving a PBS buffer including 10% DMSO (sigma) to provide compound 1 (Trichodermin) in concentrations of 50 µM, 10 µM, 5 µM, and 1 µM and compound 2 (Trichoderminol) in concentrations of 2000 µM, 1000 µM, 500 µM, and 100 µM. After each compound sample was mixed with 200 µl of the inoculum and reacted for 30 minutes at room temperature, it was inoculated. Inoculation was carried out by spraying carborundum onto 4 lower leaves including cotyledon of 4-week cultivated *Nicotiana benthamiana* and then rubbing the leaves with a mixture of the inoculum and each compound sample. This was performed at least 3 times. A mixture of DMSO and the inoculum was used as control. Spread of the pepper mottle virus was observed by detecting the green fluorescent protein under UV for 2 weeks. The plant upper leaves were harvested and taken an UV image at 3, 6, 9, 12 dpi (days post-inoculation). RNA and protein were isolated from the plant upper leaves using phenol/chloroform extraction and then RT-PCR and western blot were performed.

The following experiments was performed for RT-PCR. Each RNA sample and distilled water were added into a reaction mixture of 0.5 mM dNTPs, 10 µM reverse primer, 1× reaction buffer and 2.5 units RevertAid reverse transcriptase (Thermo scientific, USA) to be the total volume of 20 µl. RT reaction was performed by reacting the reaction mixture at 42° C. for 60 minutes using My Cycler™ Thermal Cycler (Bio-Rad, USA) (production of cDNA). The cDNA prepared from the RT reaction and distilled water were then added to a reaction mixture of 1× reaction buffer, 5 units Ex-Taq polymerase (TAKARA, Japan), 10 µM reverse primer and 10 µM forward primer to be the total volume of 30 µl. PCR was performed using My Cycler™ Thermal Cycler. [After denaturation at 95° C. for 3 minutes, it was cycled at 95° C. for 30 seconds, 58° C. for 30 seconds, and 72° C. for 60 seconds 35 times, PepMoV-CP forward primer: 5'-AGC AGC TCA AGA TCA GAC AC 3', (SEQ ID NO: 1); PepMoV-CP reverse primer: 5'-CAT ATT TCT GAC CCC AAG CAG-3', (SEQ ID NO: 2). The reaction produced from this process was performed for agarose gel electrophoresis and dyed with ethidium bromide to determine a RNA coding region of a coat protein of the pepper mottle virus (822 bp).

The following experiments was performed for western blot. Each protein sample was performed for sodium dodecyl sulfate (SDS)-polyacrylamide gel electrophoresis and the result was electro blotted and transferred to a nitrocellulose membrane using a Mini-Pro-electrophoresis system (Bio-Rad, USA). After transferring, the nitrocellulose membrane was rinsed with a TBS-T buffer (20 mM Tris(pH 7.5) and 150 mM NaCl, 0.1% Tween 20) 3 times and immersed into 5% skim milk (Difco, USA) at 25° C. for 4 hours for blocking. The nitrocellulose membrane was sequentially reacted with an antibody for the pepper mottle virus (1:1000 dilution, immunoglobulin G (Ig G) fraction, 1 mg/mL) and an alkaline phosphatase (AP)-conjugated secondary antibody (1:7500 dilution, Promega, USA), rinsed with the TBS-T buffer 3 times, and immersed into an APsubstrate buffer (0.1 M Tris (pH 9.5), 0.1 mM NaCl, 50 mN $MgCl_2$) to determine expression of the coat protein of the pepper mottle virus. The nitrocellulose membrane was dyed with western blue (Promega, USA) and compared with comigrated blue marker protein to determine position of the coat protein of the pepper mottle virus (33 kDa).

Figure 1:
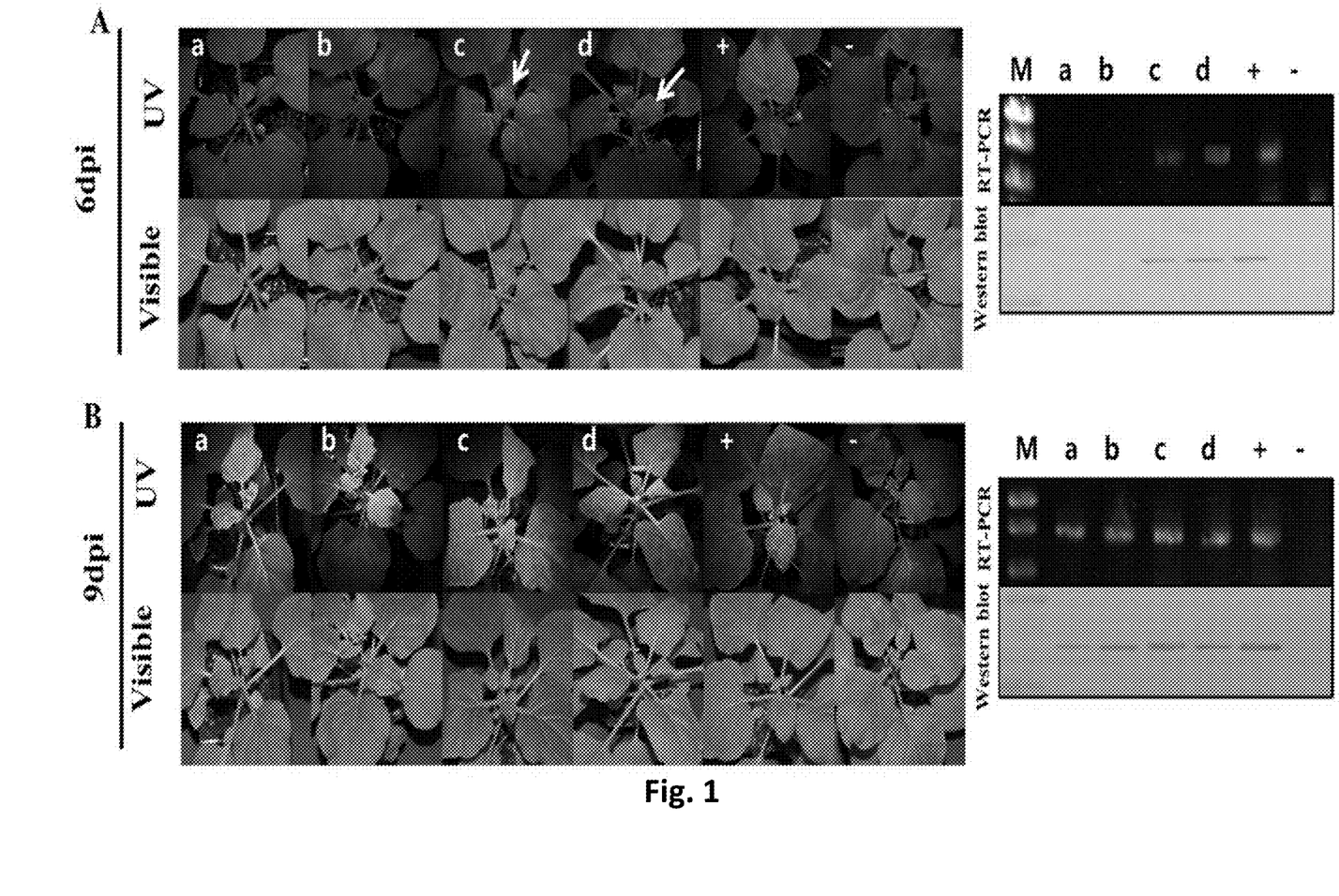
FIG. 1 illustrates an anti-viral activity of Trichodermin against a pepper mottle virus in *Nicotiana benthamiana* (A: UV image, B: RT-PCR and Western blot, a: 50 μM, b: 10 μM, c: 5 μM, d: 1 μM, +: control, −: non-treatment, M: marker).
Figure 2:
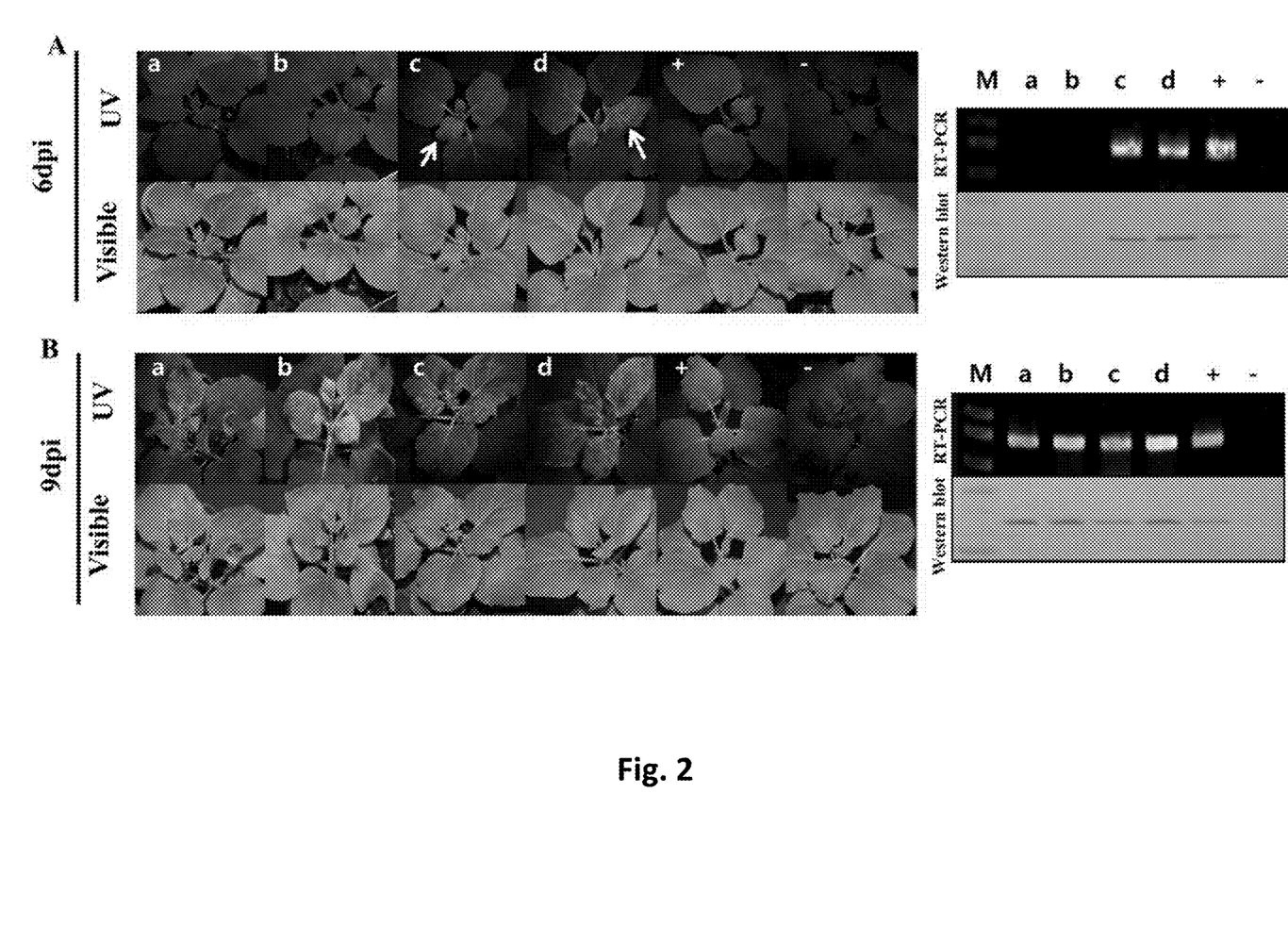
FIG. 2 illustrates an anti-viral activity of Trichoderminol against a pepper mottle virus in *Nicotiana benthamiana* (A: UV image, B: RT-PCR and Western blot, a: 2000 μM, b: 1000 μM, c: 500 μM, d: 100 μM, +: control, −: non-treatment, M: marker).

The result is summarized in FIG. 1 and FIG. 2.

As shown in FIG. 1 and FIG. 2, the green fluorescent protein was observed later with the *Nicotiana benthamiana* upper leaf samples treated with Trichodermin or Trichoderminol than the control. Viral RNA and coat protein of the pepper mottle virus were not shown for the *Nicotiana benthamiana* upper leaf samples in which the green fluorescent protein was not observed. Accordingly, it is noted that Trichodermin or Trichoderminol inhibits spreading rate of the pepper mottle virus in *Nicotiana benthamiana*.

Example 3-3. Analysis of Anti-Viral Activity in *Capsicum anuum* L

The following experiment was carried out to determine an anti-viral activity of the compounds prepared in Example 2 against the pepper mottle virus. *Capsicum anuum* L., which is a main damaged plant by the pepper mottle virus among Solanaceae plants, was used as a host plant. Cultivation, inoculum and inoculation were performed by the same methods used in Example 3-2. The result is summarized in FIG. 3.

Figure 3:
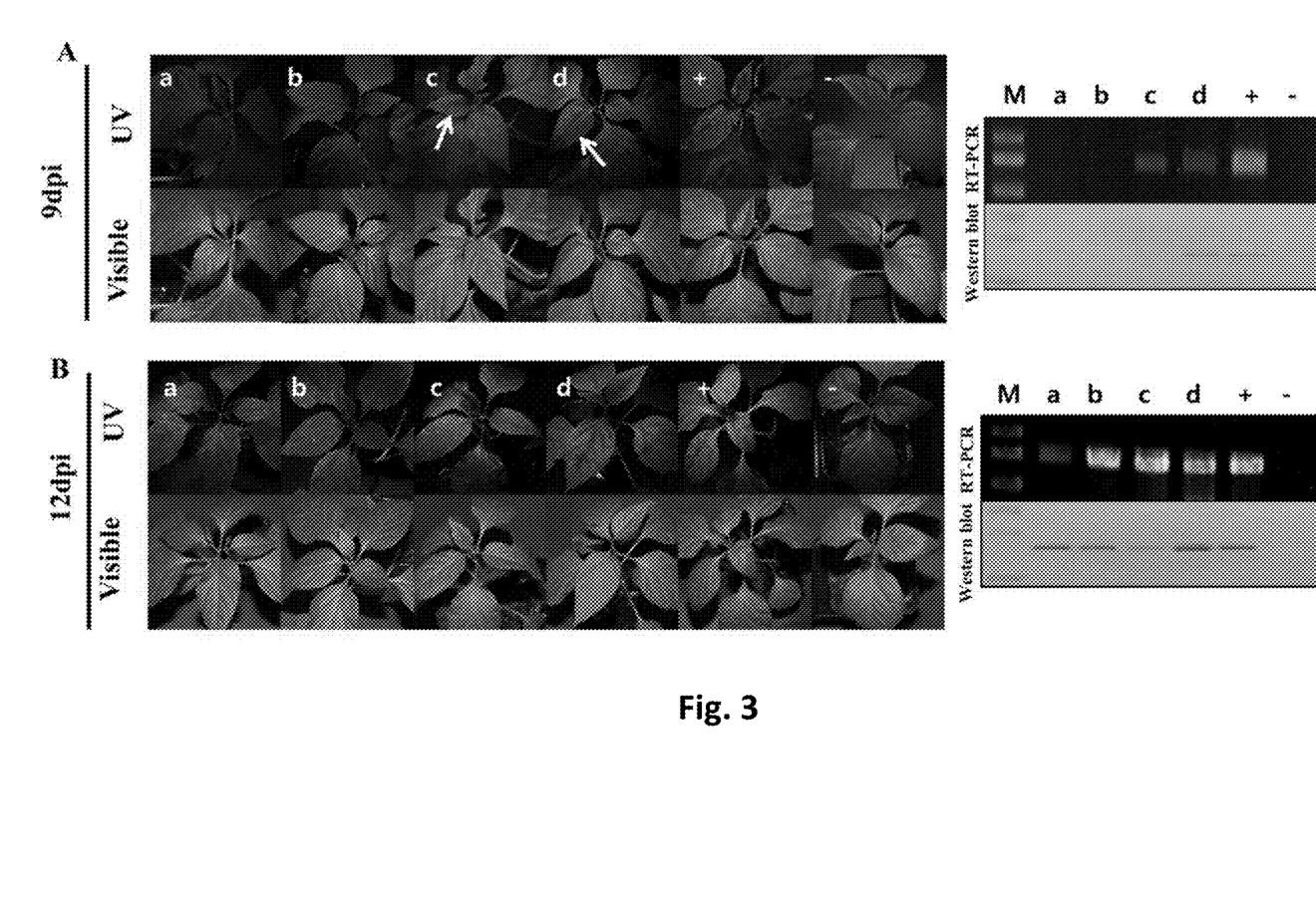
FIG. 3 illustrates an anti-viral activity of Trichodermin against a pepper mottle virus in *Capsicum anuum* L. (A: UV image, B: RT-PCR and Western blot, a: 2000 μM, b: 1000 μM, c: 500 μM, d: 100 μM, +: control, −: nontreatment, M: marker).

As shown in FIG. 3, the green fluorescent protein was observed later with the *Capsicum anuum* L. upper leaf samples treated with Trichodermin than the control. Viral RNA and coat protein of the pepper mottle virus were not shown for the *Capsicum anuum* L. upper leaf samples in which the green fluorescent protein was not observed. Accordingly, it is noted that Trichodermin inhibits spreading rate of the pepper mottle virus in *Capsicum anuum* L.

Example 4. Analysis of Anti-Viral Activity Against Tobacco Mosaic Virus

A half leaf method was performed to determine an anti-viral activity against tobacco mosaic virus, which was provided from the plant virus genebank (PVGB), Seoul women's university, of the compounds which was determined to have the anti-viral activity against the pepper mottle virus in Example 3. The half leaf method utilizes features of producing black spots due to local lesions around the infected part by tobacco mosaic virus in *Nicotiana tabacum* cv. Xanthi nc which is a local lesion host. Top 3 leaves and 4 leaves of 7-8 normal leaves of the local lesion host were taken and carborundum was evenly sprayed throughout the leaves. A compound 1 (Trichodermin) sample at test concentrations dissolved in DMSO and the tobacco mosaic virus solution were mixed. Right half leaf of the leaf of the *Nicotiana tabacum* cv. Xanthi nc was inoculated with this mixture and the other left half leaf was inoculated with tobacco mosaic virus solution (control) using cotton swabs. After petiole of the leaf of the *Nicotiana tabacum* cv. Xanthi nc was wrapped with cotton wool and distilled water was applied, it was placed in a petri dish (150 mm×2 cm) and cultivated in an incubator (no air circulation) at 23° C. for 3 days. About 1 ml of distilled water was supplied once a day to prevent drying of the leaf. After 3 days of inoculation, the number of local lesions was counted and 100-400 of lesions of uninfected control half leaf was only applied. Activity rate using the number of lesions was calculated by the following equation.

Control rate (%)=[1−(the number of lesions in infected half leaves/the number of lesions in uninfected half leaves)]×100

Figure 4:
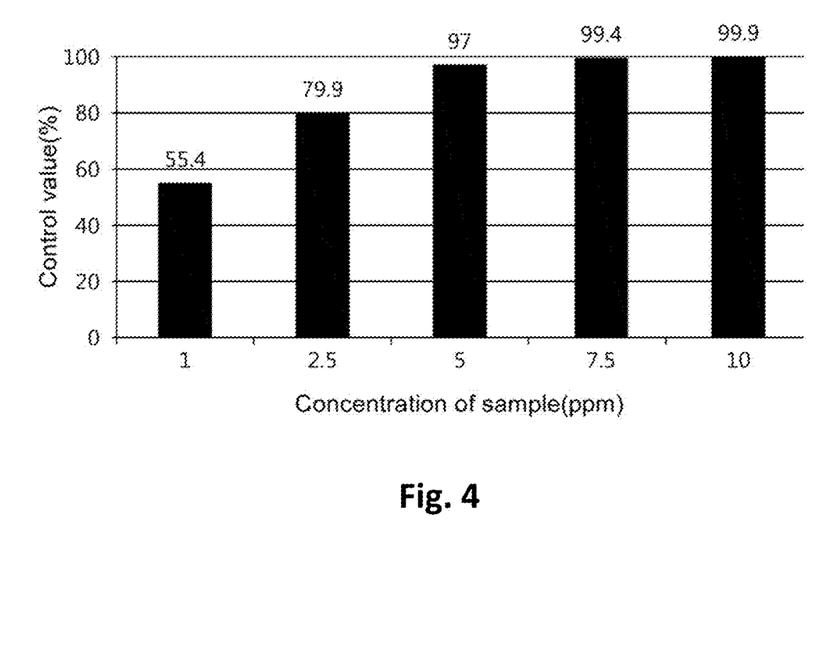
FIG. 4 illustrates an anti-viral activity of Trichodermin against a tobacco mosaic virus in *Nicotiana tabacum* cv. Xanthi nc.

The result is summarized in FIG. 4.

As shown in FIG. 4, Trichodermin shows high anti-viral activity against the tobacco mosaic virus of about 97% or above at a concentration of 5 ppm or above.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A method for controlling plant viruses comprising treating plant or soil with a composition for controlling plant viruses comprising Trichodermin represented by the following Formula 1:

Formula 1 wherein the composition has antiviral activity against plant viruses when applied to a plant or to soil,
wherein the plant virus is at least one selected from the group consisting of a tobacco mosaic virus (TMV) and a pepper mottle virus (PepMoV).

2. The method of claim 1, wherein the Trichodermin is isolated from a *Trichoderma albolutescens* strain.

3. The method of claim 2, wherein the *Trichoderma albolutescens* strain is *Trichoderma albolutescens* albolutescenes KUC21115 strain, Deposit No. KACC93215P.

4. The method of claim 1, wherein the composition is formulated into at least one selected from the group consisting of solutions, granules, powders, emulsions, oil solutions, wettable powders and pastes.

5. The method of claim 1, wherein the composition comprises a microbial cell or a culture medium of *Trichoderma albolutescens*, or a mixture thereof.

6. The method according to claim 5, wherein the microbial cell or a culture medium of *Trichoderma albolutescens* comprises *Trichoderma albolutescens* KUC21115 KUC2115 strain, Deposit No. KACC93215P.

7. The method of claim 1, wherein a concentration of the Trichodermin in the composition is 5 ppm or above.

\* \* \* \* \*